(12) United States Patent
Podolski et al.

(10) Patent No.: US 7,737,185 B2
(45) Date of Patent: Jun. 15, 2010

(54) **METHODS AND COMPOSITIONS WITH *TRANS*-CLOMIPHENE**

(75) Inventors: Joseph S. Podolski, The Woodlands, TX (US); Ronald Wiehle, Houston, TX (US)

(73) Assignee: Repros Therapeutics Inc., The Woodlands, TX (US)

( * ) Notice: Subject to any disclaimer, the term of this patent is extended or adjusted under 35 U.S.C. 154(b) by 253 days.

(21) Appl. No.: 11/750,190

(22) Filed: May 17, 2007

(65) Prior Publication Data

US 2007/0249726 A1    Oct. 25, 2007

Related U.S. Application Data

(63) Continuation-in-part of application No. 10/427,768, filed on Apr. 30, 2003, now Pat. No. 7,368,480, which is a continuation-in-part of application No. PCT/US02/21524, filed on Jul. 9, 2002.

(60) Provisional application No. 60/304,313, filed on Jul. 9, 2001.

(51) Int. Cl.
*A61K 31/135* (2006.01)
*A61P 11/00* (2006.01)

(52) U.S. Cl. .................................................. 514/651

(58) Field of Classification Search ........................ None
See application file for complete search history.

(56) References Cited

U.S. PATENT DOCUMENTS

| | | |
|---|---|---|
| 4,061,733 A | 12/1977 | Gunjikar |
| 4,820,736 A | 4/1989 | Jensen et al. |
| 4,894,373 A | 1/1990 | Young |
| 5,728,688 A | 3/1998 | Labrie |
| 5,861,389 A | 1/1999 | Radlmaier |
| 6,017,964 A | 1/2000 | MacLean et al. |
| 6,096,338 A | 8/2000 | Lacy |
| 6,126,969 A | 10/2000 | Shah |
| 6,129,933 A | 10/2000 | Oshlack |
| 6,143,353 A | 11/2000 | Oshlack |
| 6,190,591 B1 | 2/2001 | Van Lengerich |
| 6,221,399 B1 | 4/2001 | Rolfes |
| 6,248,363 B1 | 6/2001 | Patel |
| 6,291,505 B1 | 9/2001 | Huebner et al. |
| 6,342,250 B1 | 1/2002 | Masters |
| 6,391,920 B1 | 5/2002 | Fisch |
| 6,583,129 B1 | 6/2003 | Mazer et al. |
| 6,600,010 B2 | 7/2003 | Mao et al. |
| 6,638,528 B1 | 10/2003 | Kanios |
| 6,645,974 B2 | 11/2003 | Hutchinson et al. |
| 6,653,297 B1 | 11/2003 | Hodgen |
| 6,685,957 B1 | 2/2004 | Bezemer et al. |
| 6,743,448 B2 | 6/2004 | Kryger |
| 7,105,679 B2 | 9/2006 | Kanojia et al. |
| 2002/0120012 A1 | 8/2002 | Fisch |
| 2002/0183296 A1 | 12/2002 | Dudley et al. |
| 2004/0097597 A1 | 5/2004 | Podolski et al. |
| 2004/0171697 A1 | 9/2004 | Podolski et al. |
| 2004/0220154 A1 | 11/2004 | Kryger |
| 2004/0241224 A1 | 12/2004 | Podolski et al. |
| 2006/0269611 A1 | 11/2006 | Steiner et al. |

FOREIGN PATENT DOCUMENTS

| | | |
|---|---|---|
| AU | 2001261684 | 12/2001 |
| EP | 0206021 A | 8/1988 |
| EP | 0430388 A2 | 6/1991 |
| EP | 0888775 A2 | 7/1999 |
| EP | 1829534 A1 | 3/2006 |
| JP | 4-312522 | 11/1992 |
| WO | WO 95/35093 | 12/1995 |
| WO | WO 01/34117 A1 | 5/2001 |
| WO | WO 01/91744 A1 | 12/2001 |
| WO | WO 03/005954 A2 | 1/2003 |
| WO | WO 03/005954 A3 | 1/2003 |
| WO | WO 03/026568 A2 | 4/2003 |
| WO | WO 03/072092 | 9/2003 |
| WO | WO 2006/019916 | 2/2006 |
| WO | WO 2006/084153 | 8/2006 |
| WO | WO 2006/102232 | 9/2006 |
| WO | WO 2007/019165 | 2/2007 |
| WO | WO 2009/051908 | 4/2009 |

OTHER PUBLICATIONS

Laghi et al. (Am J Respir Crit Care, Med vol. 171, pp. 598-605, 2005).*
Debigare et al. (Am. J. Respir. Crit. Care Med., vol. 165, No. 9, 2001, pp. 1712-1717).*
Casaburi et al. (Am J Respir Crit Care Med. vol. 170, pp. 870-878, 2004).*
Banner A. S. (Lancet, vol. 354, Aug. 7, 1999, pp. 440-441).*
Vippagunta (Adv. Drug Del. Rev., 2001, vol. 48, 2001, pp. 3-26.*
ACCE Clinical Practice Guidelines for the Evaluation and Treatment of Hypogonadism in Adult Male Patients (1996).

(Continued)

*Primary Examiner*—Brian-Yong S Kwon
(74) *Attorney, Agent, or Firm*—Howrey LLP

(57) ABSTRACT

The present invention relates to the use of compositions comprising trans-clomiphene for treating wasting, especially a loss of muscle mass. The invention is also directed to methods for treating wasting in a patient with chronic obstructive pulmonary disorder. The present invention is also directed to methods for treating hypogonadism in males with chronic obstructive pulmonary disorder.

7 Claims, 6 Drawing Sheets

OTHER PUBLICATIONS

Agarwal, et al., "Male Sexual Dysfunction After Stroke," J Assoc. Physicians India, vol. 37, No. 8, pp. 505-507 (1989).

Barg, P., et al., "Male Factor: Clinical Evaluation of the Semen Analysis," Infert. Reprod. Med. Clin. North Amer., vol. 2, pp. 333-340 (1991).

Bartsch, G., "The Effect of Antiestrogen, Antiandrogen, and the Prolactin Inhibitor 2 Bromo-'alpha!-ergocriptine on the Stromal Tissue of Human Benign Prostatic Hyperplasia. Correlation of Sterological Data and Plasma Hormones," Database Embase; Elsevier Science Publishers, Amsterdam, NL, 1981, vol. 18, No. 4, pp. 308-312.

Bhasin, S., et al., J. Clin Endocrin, Metabol., vol. 91, pp. 1995-2010 (2006).

Brody, J., "Sperm Found Especially Vulnerable to Environment," The New York Times, Mar. 10, 1981.

Broulik, P.D., "Tamoxifen Prevents Bone Loss in Castrated Male Mice," Hormone and Metabolic Research, Thieme-Stratton, Stuttgart, DE, vol. 32, No. 5, pp. 181-184 (2000) XP009041862.

Burghardt, et al., "Gap Junction Modulation in Rat Uterus. III. Structure-Activity Relationships of Estrogen Receptor-Binding Ligands on Myometrial and Serosal Cells," Biol. Reprod. vol. 36, No. 3, pp. 741-751 (1977).

Chang, Ching-Fong, et al., Aquaculture, vol. 101, pp. 329-36 (1992).

Drew, A., "Letter: Possible Teratogenic Effect of Clomifene," Developmental Medicine and Child Neurology, vol. 16, No. 2, pp. 276 (1974).

Editions Du Vidal Ed - Editions Du Vidal: Vidal 1997; Dictionnaire Vidal 1997, Paris, FR, p. 1161 XP002150196.

Eil, "Ketoconazole Binds to the Human Androgen Receptor," Harm Metab Res., vol. 24, No. 8, pp. 367-370 (1992).

Elanjian, Sona I., "Clomiphene for Male Infertility," Journal of Pharmacy Technology, vol. 12, No. 3, pp. 102-104 (1996).

EP Supplementary Search Report of EP 02748104 dated Jun. 24, 2005.

EP Supplementary Search Report of EP 06720243 dated Aug. 6, 2008.

EP Supplementary Search Report of EP 06738985 dated Aug. 15, 2008.

EP Supplementary Search Report of EP 06800648 dated Jul. 21, 2008.

Epstein, "Clomiphene Treatment in Oligospermic Infertile Males," Fertility and Sterility, vol. 28, No. 7, pp. 741-745 (1977).

Excerpt on www.medscape.com from Drug Ther. Perspect., vol. 10, pp. 1-5 (1997).

Garg, Abhimanyu, "Medical progress: Acquired and Inherited Lipodystrophies," New England Journal of Medicine, vol. 35, No. 12, pp. 1231-1232 (2004).

Glasier, A., et al., "A Comparison of the Effects on Follicular Development Between Clomiphene Citrate its Two Separate Isomers and Spontaneous Cycles," Human Reproduction, vol. 4, No. 3, pp. 252-256 (1989).

Grinenko, et al., Khimiko-farmatsevticheskii Zhurnal, vol. 23, No. 1, pp. 123-126 (1989).

Guay, A., et al., Internet!. J. Ompot. Res., vol. 15, pp. 156-165 (2003).

Guzick, D., et al., "Sperm Morphology, Motility and Concentration in Fertile and Infertile Men," N. Engl. J. Med., vol. 345, pp. 1388-1393 (2001).

Hanus, M., et al., "Antiestrogens (Tamoxifen) in the Alternative Therapy of Benign Prostatic Hyperplasial," US National Library of Medicine, Bethesda, MD, Databse Medline, vol. 72, No. 7, pp. 316-318 (1993).

Hayashi, Norio, et al., Hinyokika Kiyo (Acta Urologica Japonica), vol. 34, No. 5, pp. 847-50 (1988) with English translation.

Herzog, A. G., "Reproductive Endocrine Considerations and Hormonal Therapy for Men with Epilepsy," Epilepsia, Raven Press Ltd., New York, US (1991), vol. 32, No. Suppl. 6, pp. S34-S37.

International Preliminary Examination Report of PCT/US02/21524 dated Mar. 3, 2006.

International Preliminary Report on Patentability of PCT/US05/02500 dated Jan. 16, 2007.

International Preliminary Report on Patentability of PCT/US06/003882 dated Aug. 7, 2007.

International Preliminary Report on Patentability of PCT/US06/030053 dated Feb. 5, 2008.

International Preliminary Report on Patentability of PCT/US06/10022 dated Sep. 25, 2007.

International Search Report of PCT/US02/21524 dated Jun. 18, 2003.

International Search Report of PCT/US06/003882 dated Aug. 14, 2006.

International Search Report of PCT/US06/10022 dated Jan. 10, 2007.

International Search Report of PCT/US06/30053 dated Dec. 22, 2006.

International Search Report of PCT/US08/075433 dated Dec. 19, 2008.

International Search Report of PCT/US09/063621 dated Dec. 28, 2009.

Jones, T. Hugh., "Testosterone Associations with Erectile Dysfunction, Diabetes, and the Metabolic Syndrome," European Urology Supplements, vol. 6, pp. 847857 (2007).

Kadioglu, et al., Treatment of Idiopathic and Postvaricocelectomy Oligozoospermia with Oral Tamoxifen Citrate, BJU Int., vol. 83, No. 6, pp. 646-648 (1999).

Ke, H. Zhu, et al., "Lasofoxifene, A Selective Estrogen Receptor Modulator, Prevents Bone Loss Induced by Aging and Orchidectomy in the Adult Rat," Endocrinology, vol. 141, No. 4, pp. 1338-1344 (2000) XP001170303.

Kidd, S., et al., "Effects of male age on semen quality and fertility: a review of the literature," Fertility and Sterility, vol. 75, pp. 237-248 (2001).

Kotoulas, et al., "Tamoxifen Treatment in Male Infertility. I. Effect on spermatozoa," Fertil. Steril., vol. 61, No. 5, pp. 911-914 (1994).

Lewis, B., et al., "Medical Implication of the Biological Clock," JAMA, vol. 296, pp. 2369-2371 (2006).

Lim, V., et al., "Restoration of Plasma Testosterone Levels in Uremic Men with Clomiphene Citrate," Journal of Clinical Endocrinology and Metabolism, New York, US vol. 43, No. 6, pp. 1370-1377 (1976) XP 009041861.

Lund, et al., "Testosterone and Andropause: the Feasibility of Testosterone Replacement Therapy in Elderly Men," Pharmacotherapy, vol. 19, No. 8, pp. 951-956 (1999).

Macleod, J., et al., J. Urology, vol. 66, pp. 436-449 (1951).

McKinlay, et al., "The Questionable Physiologic and Epidemiologic Basis for a Male Climacteric Syndrome: Preliminary Results from the Massachusetts Male Aging Study," Maturitas, vol. 11, No. 2, pp. 103-115 (1989).

PCT Written Opinion of PCT/US05/02500 dated Sep. 14, 2006.
PCT Written Opinion of PCT/US06/003882 dated Aug. 4, 2007.
PCT Written Opinion of PCT/US06/10022 dated Jan. 10, 2007.
PCT Written Opinion of PCT/US06/30053 dated Dec. 22, 2006.
PCT Written Opinion of PCT/US08/075433 dated Dec. 19, 2008.
PCT Written Opinion of PCT/US09/063621 dated Dec. 28, 2009.

Petak, S., et al., American Association of Clinical Endocrinologists Medical Guidelines for Clinical Practice for the Evaulation and Treatment of Hypogonadism in Adult Male Patients, Endocrine Practice, vol. 8, pp. 439-456 (2002).

Ronnberg, "The Effect of Clomiphene Treatment on Different Sperm Parameters in Men with Idiopathic Oligozoospermia," Andrologia, vol. 12, No. 1, pp. 261-265 (1980).

Schultheiss, D., et al., "Testosterone Therapy in the Ageing Male: What About the Prostate?" Andrologia, vol. 36, No. 6, pp. 357-365 (2004).

Schweikert, et al., "Effects of Estrogen Deprivation on Human Benign Prostatic Hyperplasia," Steroid Biochem Mol Biol., vol. 44, No. 4-6, pp. 573-576 (1993).

Shamis, et al., Arch. Androl., vol. 21, pp. 109 (1991).

Shirai, Takashi, et al., Saishin-Igaku (Latest Medical Science), vol. 45, No. 11, pp. 2250-2254 (1990) with English translation.

Sokel, Fertil and Steril, vol. 49, pp. 865 (1988).

Stahl, F., et al., "Effects of Tamoxifen on the Levels of luteinizing Hormone (LH), Follicle Stimulating Hormone FSH), Prolactin (PRL), 17 beta-oestradiol (E2), and free dihydrotestosterone (DHT)

in blood of patients with Benign Prostatic Hyperplasia," US National Library of Medicine, Bethesda, MD, US, vol. 82, No. 1, pp. 21-28 (1983).

Stedman's Medical Dictionary, William and Wilking, pp. 1312, 1439 & 1798-1799 (1995).

Steiner, et al., "Antiestrogens and Selective Estrogen Receptor Modulators Reduce Prostte Cancer Risk," World J Urol., vol. 21, pp. 31-36 (2003).

Sterochemistry of Geometric Isomers of Clomiphene: a Correction of the Literature and a Reexamination of Structure-Activity Relationships, Journal of Pharmaceutical Science, vol. 65, No., pp. 184-150 (176) XP009056304.

Takihara, Hiroshi, Jin to Toseki (Kidney and Dialysis) vol. 41, Special Edition, pp. 759-61 (1996) with English translation.

Tenover, J., et al., J Clin. Endocrine. Metabol., vol. 75, pp. 1092-1098 (1992).

Tenover, J., et al., "Male Hormone Replacement Therapy Including Andropause," Endocrinology and Metabolism Clinics of North America, W.B. Saunders Company, Philadelphia, US, Dec. 1998, vol. 27, No. 4, pp. 969-987 XP008019800.

Weissenberg, R., et al., "The Effect of Clomiphene Citrate and is Zu or En isomers on the Reproductive System of the Immature Male Rate," Andrologia, vol. 24, pp. 161-165 (1992).

Written Opinion of Singapore Patent Applc. 2007-05640-1 dated Jul. 9, 2008.

U.S. Appl. No. 10/427,768 Examiners Interview Summary Record dated Nov. 19, 2007.

U.S. Appl. No. 10/427,768 Final office action dated Apr. 6, 2006.

U.S. Appl. No. 10/427,768 Non-final office action dated May 29, 2007.

U.S. Appl. No. 10/427,768 Non-final office action dated Oct. 12, 2005.

U.S. Appl. No. 10/427,768 Notice of Allowance and Examiner's Amendment dated Dec. 27, 2007.

U.S. Appl. No. 10/427,768 Restriction Requirement dated May 23, 2005.

U.S. Appl. No. 10/483,458 Non-final office action dated Jul. 20, 2009.

U.S. Appl. No. 10/483,458 Advisory Action dated Jan. 16, 2009.

U.S. Appl. No. 10/483,458 Final office action dated Nov. 19, 2008.

U.S. Appl. No. 10/483,458 Non-final office action dated Feb. 13, 2008.

U.S. Appl. No.10/483,458 Restriction Requirement dated Oct. 25, 2007.

U.S. Appl. No. 10/712,546 Non-final office action dated Mar. 15, 2006.

U.S. Appl. No. 10/712,546 Notice of Allowance dated Sep. 29, 2006.

U.S. Appl. No. 10/712,546 Restriction Requirement dated Nov. 10, 2005.

U.S. Appl. No. 11/571,150 Restriction Requirement dated Aug. 31, 2009.

U.S. Appl. No. 11/571,150 Non-final office action dated Oct. 14, 2009.

U.S. Appl. No. 11/997,858 Restriction Requirement dated Aug. 28, 2009.

U.S. Appl. No. 11/815,542 Restriction Requirement dated Aug. 31, 2009.

U.S. Appl. No. 11/815,542 Non-final office action dated Oct. 15, 2009.

U.S. Control No. 90/008,024 Non-final office action dated Nov. 1, 2006.

U.S. Control No. 90/008,024 Examiner Interview Summary Record dated Dec. 13, 2006.

U.S. Control No. 90/008,024 Non-final office action dated Jan. 29, 2007.

U.S. Control No. 90/008,024 Final office action dated Jun. 22, 2007.

U.S. Control No. 90/008,024 Examiner Interview Summary Record dated Jul. 25, 2007.

U.S. Control No. 90/008,024 Final office action dated Nov. 16, 2007.

U.S. Control No. 90/008,024 Advisory Action dated Feb. 1, 2008.

U.S. Control No. 90/008,024 Advisory Action dated Mar. 5, 2008.

U.S. Control No. 90/008,024 Examiners Answer dated Jun. 12, 2008.

U.S. Control No. 90/006,921 Non-final office action dated Sep. 9, 2004.

U.S. Control No. 90/006,921 Examiners Interview Summary dated Oct. 20, 2004.

U.S. Control No. 90/006,921 Final office action dated Feb. 23, 2005.

U.S. Control No. 90/006,921 Petition Decision dated May 25, 2005.

U.S. Control No. 90/006,921 Non-final office action dated Jun. 27, 2005.

* cited by examiner

Normal Secretory Total Serum Testosterone Profiles in Healthy Young and Older Men

METHODS AND COMPOSITIONS WITH *TRANS*-CLOMIPHENE

This application is a continuation-in-part of U.S. application Ser. No. 10/427,768, filed Apr. 30, 2003, now U.S. Pat. No. 7,368,480 which is a continuation-in-part of International Application No. PCT/US02/021524, filed Jul. 9, 2002, which claims the benefit, under 35 U.S.C. §119(e), of U.S. Provisional Patent Application No. 60/304,313, filed on Jul. 9, 2001. All applications are incorporated herein by reference in their entirety.

BACKGROUND

1. Field of the Invention

The present invention relates to compositions and methods for treating wasting. More specifically, the present invention relates to treatments for increasing muscle mass in individuals with chronic obstructive pulmonary disease. The present invention also relates to the use of a composition comprising clomiphene enriched for trans-clomiphene reagents for treating hypogonadism, preferably secondary hypogonadism, in individuals with chronic obstructive pulmonary disease.

2. Description of Related Art a. Testosterone

Testosterone is the primary male androgen, playing a vital role in overall male health. Testosterone is essential to the development and maintenance of specific reproductive tissues (testes, prostate, epididymis, seminal vesicle and penis) and male secondary sex characteristics. It plays a key role in libido and erectile function and is necessary for the initiation and maintenance of spermatogenesis. Testosterone also has important functions not related to reproductive tissues. For example, it positively affects body composition by increasing nitrogen retention, which supports lean body mass, muscle size and strength. It also acts on bone to stimulate bone formation.

Testosterone deficiency can result from disease or genetic disorders and is also frequently a complication of aging. Some of the sequelae of adult testosterone deficiency include a wide variety of symptoms including: loss of libido, erectile dysfunction, oligospermia or azoospermia, absence or regression of secondary sexual characteristics, progressive decrease in muscle mass, fatigue, depressed mood and increased risk of osteoporosis.

Several forms of testosterone therapy exist in the United States today. Recently, transdermal preparations have gained favor in the market. However, a scrotal testosterone patch results in supraphysiological levels of 5α-dihydrotestosterone (DHT) due to the high concentration of 5α-reductase in scrotal skin. Elevated DHT levels may have pernicious effects on the prostate over time. Nonscrotal systems are considered more convenient and most patients achieve average serum concentrations within the normal range and have normal levels of DHT. Oral testosterone therapy is not recommended because doses required for replacement therapy are associated with significant risk of hepatotoxicity.

b. Chronic Obstructive Pulmonary Disease

Chronic obstructive pulmonary disease (COPD) is a progressive lung disease characterized by a gradual and irreversible loss of lung function. COPD includes two related lung diseases: chronic bronchitis and emphysema. Chronic bronchitis is an inflammation and eventual scarring of the bronchial tubes. Emphysema is the loss of elasticity of lung tissue and destruction of alveoli-supporting structures and alveoli-feeding capillaries within the lungs. Persons with COPD have difficulty breathing due to smaller air passageways and partially destroyed alveoli. Additionally, the air passageways of persons with COPD become clogged with mucus. COPD represents the fourth leading cause of death in the United States, where 14 million people have been diagnosed with the disease. The most important risk factor for COPD is cigarette smoking.

Muscle wasting is prevalent in a large population of patients with COPD, and it is estimated that over 50% of COPD patients experience some loss of fat-free muscle. Loss of muscle mass adversely affects respiratory and peripheral muscle function, exercise capacity and health status and is a demonstrated predictor of mortality in COPD patients. Gain in muscle mass and strength, on the other hand, is associated with increased exercise capacity and survival. Muscle wasting in persons with COPD does not appear to result primarily from inadequate nutritional intake. Similar to cachexia, preferential loss of muscle tissue over fat, unresponsiveness to nutritional intervention and enhanced protein degradation are observed in persons with COPD.

On the basis of the chronicity of COPD and the elevated age of most COPD patients, it has been suggested that men with COPD may be at risk for hypogonadism. Importantly, low testosterone levels have been observed in patients with COPD, especially those undergoing glucocorticosteroid therapy and significant atrophy of Leydig cells has been observed in some COPD patients. However, it is currently unclear to what extent COPD contributes to the observed decreased testosterone levels.

Numerous studies suggest that hormones may play a role in weight loss and wasting. Androgen supplementation therapy, directed at curing dysfunction of the peripheral muscles in COPD patients, has been the subject of several controlled studies. Positive effects on fat-free mass and overall weight gain in COPD patients were reported in these studies. At least one study also reported improvements in muscle function and exercise capacity.

The aforementioned studies indicate the usefulness and efficacy of testosterone therapy in treating symptoms of COPD. However, high amounts of testosterone increase the risk of cardiovascular disease and benign prostate hyperplasia (BPH) and some forms of testosterone administration result in elevated levels of DHT. The association of high levels of serum DHT and BPH and the subsequent development of prostate cancer is a potential drawback to the use of testosterone gels or patches that enhance DHT.

c. Clomiphene

Clomiphene, which is an antiestrogen related to tamoxifen, has also been used to treat men with low testosterone levels. Clomiphene blocks the normal estrogen feedback on the hypothalamus and subsequent negative feedback on the pituitary. This leads to increases in luteinizing hormone (LH) and follicle stimulating hormone (FSH). In men, these increased levels of gonadotropins stimulate the Leydig cells of the testes and result in the production of higher testosterone levels.

Tenover et al., J. Clin. Endocrinol. Metab. 64:1103, (1987) and Tenover et al., J. Clin. Endocrinol. Metab. 64:1118 (1987) found increases in FSH, LH in both young and old men after treatment with clomiphene. They also found increases in free and total testosterone in men with young men showing significant increases.

Studies were also conducted to determine whether or not clomiphene could be used to improve fertility in men by improving semen quality. Homonnai et al. Fertil. and Steril 50:801 (1988) saw increases in sperm concentration and count but others have not. (See e.g., Sokel, et al., Fertil. and Steril. 49:865 (1988); Check, et al., Int. J. Fertil. 34:120

(1989); Purvis, et al., Int. J. Androl 21:109 (1989); and Breznik, Arch. Androl. 21:109 (1993).) One group saw a deterioration in the percentage of normal sperm with long-term treatment. Shamis, et al., Arch. Androl 21:109 (1991). A WHO study showed no changes in semen quality or fertility after 6 months of treatment. (Anonymous Androl. 15:299 (1992).) A meta-analysis seems to confirm that testosterone levels go up in men with poor quality sperm but not fertility. (Vanderkerckhove, et al., 2000).

Vandekerckhove, et al. (Cochrane Database Syst Rev 2000; (2):CD000151 (2000)) noted that ten studies involving 738 men have suggested that anti-estrogens appear to have a beneficial effect on endocrinal outcomes, i.e. testosterone, but there is not enough evidence to evaluate fertility effects. Nevertheless should clomiphene administration enhance testosterone levels then one could easily conclude that the drug should positively impact the side effects of testosterone deprivation as long as the testes still retain the ability to respond to gonadotropin stimulation.

Ernst et al., J. Pharmaceut. Sci. 65:148 (1976), have shown that clomiphene is a mixture of two geometric isomers which they refer to as cis, -Z-, clomiphene (cis-clomiphene or zuclomiphene) and trans-, E-, clomiphene, (trans-clomiphene or enclomiphene). According to Ernst, et al. trans-clomiphene HCI has a melting point of 149° C.-150.5° C., while cis-clomiphene HCI has a melting point of 156.5° C.-158° C. Ernst et al. have also noted that (the trans-isomer) is antiestrogenic (AE) while the cis-isomer is the more potent and more estrogenic form and has also been reported to have anti-estrogenic activity. The authors attribute the effect of the drug on ovulatory activity to both forms stating that the mixture is more effective than trans-clomiphene alone. The trans-isomer aids ovulation at the level of the hypothalamus. The estrogenic isomer cis-clomiphene contributes to enhanced ovulation elsewhere in the physiologic pathway leading to ovulation. The isomers are also reported to have different in vivo half-life. Furthermore the cis form has been reported to leave residual blood levels for in excess of one month following a single dose.

Clomiphene is currently approved as a mixture of both cis- and trans-isomers, the cis-isomer being present as about 30% to 50% (Merck Manual) for fertility enhancement in the anovulatory patient. Clomiphene improves ovulation by initiating a series of endocrine events culminating in a preovulatory gonadotropin surge and subsequent follicular rupture. The drug is recommended to be administered for 5 days at a dose of up to 100 mg daily. Clomiphene has also been associated with numerous side effects including: blurred vision, abdominal discomfort, gynecomastia, testicular tumors, vasomotor flushes, nausea, and headaches. Furthermore, other studies suggest that clomiphene possesses both genotoxic and tumor enhancement effects. The net outcome of these observations is that clomiphene in its current format, having between 30% and 50% of the cis isomer, would be unacceptable for chronic therapy.

There continues to be a need for methods of treating wasting and hypogonadism in patients with COPD which avoids the increased risk of cardiovascular disease and benign prostate hyperplasia (BPH) accompanying traditional testosterone supplementation regimens. The present invention addresses this need and provides novel compositions and methods for treating wasting and hypogonadism.

SUMMARY

The present invention relates to a composition comprising 0% to about 29% weight/weight of (cis, -Z-, trans-clomiphene) (hereinafter "cis-clomiphene") and about 100% to about 71% w/w (trans-, E-, cis-clomiphene) (hereinafter "trans-clomiphene") or analogs thereof (such as those described in Ernst, et al. supra) or pharmaceutically acceptable salts thereof. The composition may further comprise one or more pharmaceutically acceptable diluents, adjuvants, carriers or excipients.

The present invention also relates to a composition comprising cis-clomiphene and trans-clomiphene or analogs thereof or pharmaceutically acceptable salts or solvates thereof, wherein the ratio of trans-clomiphene to cis-clomiphene is greater than 71/29. The composition may further comprise one or more pharmaceutically acceptable diluents, adjuvants, carriers or excipients.

The present invention also relates to a composition consisting essentially of trans-clomiphene or analogs thereof or pharmaceutically acceptable salts or solvates thereof. The composition may further comprise one or more pharmaceutically acceptable diluents, adjuvants, carriers or excipients.

The present invention also relates to a method for treating wasting in a mammal with chronic obstructive pulmonary disease (COPD), comprising administering to the mammal an effective amount of a composition according to the present invention, the compositions having active ingredients comprising 0% to about 29% weight/weight of cis-clomiphene and about 100% to about 71% w/w trans-clomiphene or analogs thereof or pharmaceutically acceptable salts or solvates thereof. The composition may further comprise one or more pharmaceutically acceptable diluents, adjuvants, carriers or excipients. The mammal may be a male or female. The mammal may also be a human.

The present invention also relates to a method for treating wasting in a mammal with COPD, comprising administering to the mammal an effective amount of a composition comprising cis-clomiphene and trans-clomiphene or analogs thereof or pharmaceutically acceptable salts or solvates thereof, wherein the ratio of trans-clomiphene to cis-clomiphene is greater than 71/29. The composition may further comprise one or more pharmaceutically acceptable diluents, adjuvants, carriers or excipients. The mammal may be a male or female. The mammal may also be a human.

The present invention also relates to a method for treating wasting in a mammal with COPD, comprising administering to the mammal an effective amount of a composition consisting essentially of trans-clomiphene or analogs thereof or pharmaceutically acceptable salts or solvates thereof. The composition may further comprise one or more pharmaceutically acceptable diluents, adjuvants, carriers or excipients. The mammal may be a male or female. The mammal may also be a human.

The present invention also relates to a method for treating wasting in a mammal with COPD, comprising administering to the mammal an effective amount of a composition comprising an antiestrogen or an analog thereof or a pharmaceutically acceptable salt or solvate thereof. The composition may further comprise one or more pharmaceutically acceptable diluents, adjuvants, carriers or excipients. The mammal may be a male or female. The mammal may also be a human.

The present invention also relates to a method for treating hypogonadism in a male mammal with COPD, comprising administering to the mammal an effective amount of a composition according to the present invention, the compositions having active ingredients comprising 0% to about 29% weight/weight of cis-clomiphene and about 100% to about 71% w/w trans-clomiphene or analogs thereof or pharmaceutically acceptable salts or solvates thereof. The hypogonadism preferably is secondary hypogonadism. The composition may further comprise one or more pharmaceutically acceptable diluents, adjuvants, carriers or excipients. The mammal may be a human.

The present invention also relates to a method for treating hypogonadism in a male mammal with chronic obstructive pulmonary disease (COPD), comprising administering to the mammal an effective amount of a composition comprising cis-clomiphene and trans-clomiphene or analogs thereof or pharmaceutically acceptable salts or solvates thereof, wherein the ratio of trans-clomiphene to cis-clomiphene is greater than 71/29. The hypogonadism preferably is secondary hypogonadism. The composition may further comprise one or more pharmaceutically acceptable diluents, adjuvants, carriers or excipients. The mammal may be a human.

The present invention also relates to a method for treating hypogonadism in a male mammal with COPD, comprising administering to the mammal an effective amount of a composition consisting essentially of trans-clomiphene or analogs thereof or pharmaceutically acceptable salts or solvates thereof. The hypogonadism preferably is secondary hypogonadism. The composition may further comprise one or more pharmaceutically acceptable diluents, adjuvants, carriers or excipients. The mammal may be a human.

The present invention also relates to a method for treating hypogonadism in a male mammal with COPD, comprising administering to the mammal an effective amount of a composition comprising an antiestrogen or an analog thereof or a pharmaceutically acceptable salt or solvate thereof. The hypogonadism preferably is secondary hypogonadism. The composition may further comprise one or more pharmaceutically acceptable diluents, adjuvants, carriers or excipients. The mammal may be a human.

DETAILED DESCRIPTION

Figure 1:
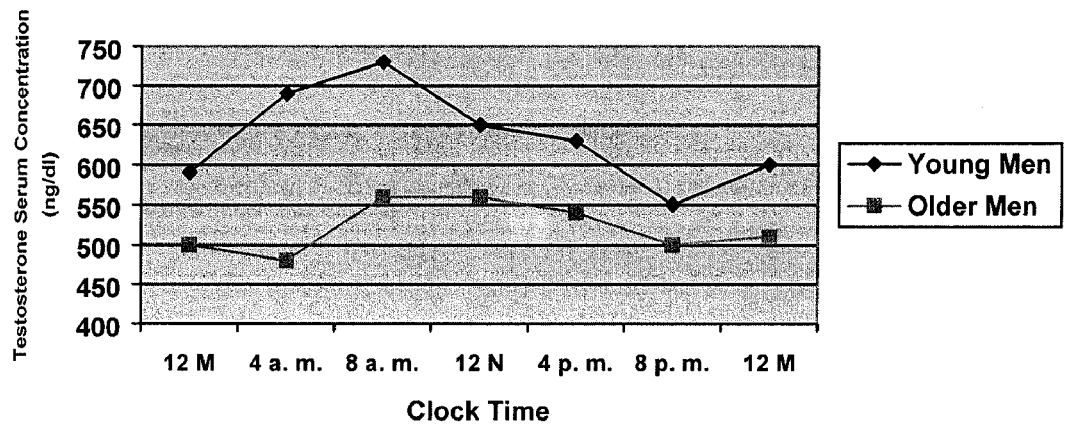
FIG. 1 is a graphic representation of the normal secretory total serum testosterone profiles in healthy men (young and old).
Figure 2:
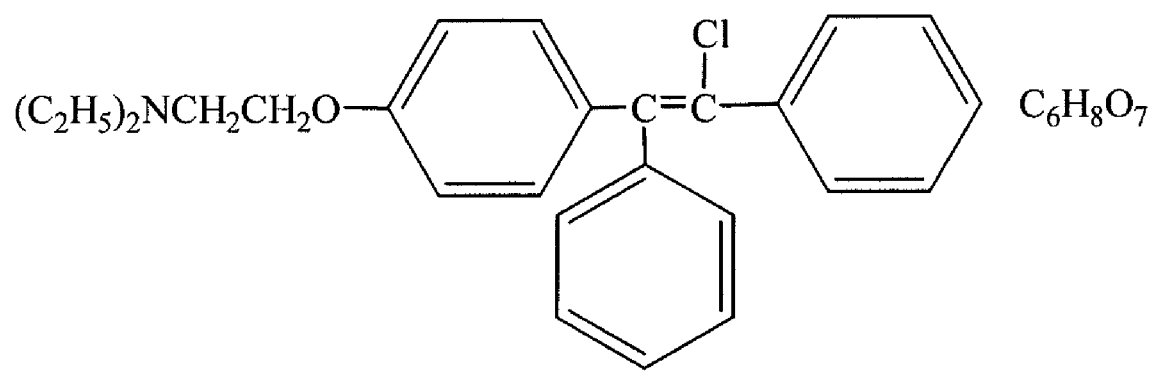
FIG. 2 shows the chemical structure of clomiphene citrate.

The present invention is directed to compositions comprising clomiphene with increased amounts of trans-clomiphene. The trans-isomer of clomiphene is an anti-estrogen, whereas the cis-isomer of clomiphene is estrogenic. By increasing the relative amount of the trans-isomer in clomiphene-containing compositions, the anti-estrogenic properties of the trans-isomer may be taken advantage of while lowering or eliminating potential side effects caused by the estrogenic cis-isomer.

In one aspect of the present invention, the composition comprises 0% to about 29% w/w of cis-clomiphene and about 100% to about 71% trans-clomiphene or analogs thereof or pharmaceutically acceptable salts or solvates thereof. In another aspect of the present invention, the composition comprises cis-clomiphene and trans-clomiphene or analogs thereof or pharmaceutically acceptable salts or solvates thereof, wherein the ratio of trans-clomiphene to cis-clomiphene is greater than 71/29. In yet another aspect of the present invention, the composition consists essentially of trans-clomiphene or analogs thereof or pharmaceutically acceptable salts or solvates thereof. In yet another aspect of the present invention, the composition comprises an antiestrogen or a pharmaceutically acceptable salt or solvate thereof. The compositions of the present invention may further comprise one or more pharmaceutically acceptable diluents, adjuvants, carriers or excipients.

The compositions of the present invention may be administered to a mammal in order to obtain beneficial effects of an antiestrogen including, but not limited to, increased levels of testosterone. Persons with COPD demonstrate low serum total or free testosterone and consequently may manifest symptoms including lack of energy, lack of libido, muscle loss and bone loss. The compositions of the present invention may be administered to a mammal for increasing or modulating muscle mass, bone density, libido, potency, body performance capacity, memory and lymphocyte levels. The compositions of the present invention may also be administered to a mammal for treating a symptom of COPD such as, without limitation, wasting and hypogonadism, preferably secondary hypogonadism.

The compositions of the present invention may be administered to any mammal that would benefit from increased levels of testosterone. The mammal may be a male or female. The mammal may be a human.

The compositions of the present invention may also be administered to a person with COPD in order to treat wasting. Testosterone supplementation has been demonstrated to increase muscle mass in males with COPD. Gain in lean body mass has been associated with decrease in all-cause mortality in patients with COPD. Compositions comprising trans-clomiphene may be used in patients with COPD as an alternative to testosterone therapy. Trans-clomiphene treatment has low liver and kidney toxicity and favorable effects on cholesterol, lipids and lymphocyte levels. Moreover, treatment with trans-clomiphene may have reduced side effects compared to testosterone therapy, such as PSA and cardiovascular risks, and importantly, treatment with trans-clomiphene does not elevate DHT levels and therefore avoids the pernicious effects of DHT levels on the prostate. Although compositions comprising trans-clomiphene are preferred, compositions comprising any antiestrogen are within the scope of the invention, so long as administration of an effective amount of the antiestrogen to a mammal elevates the mammal's serum testosterone level. Preferably, the individual with COPD is a male. More preferably, the individual with COPD is a male with serum testosterone levels below the normal range.

"Wasting" refers to catabolism and/or progressive loss of weight in a subject, or to loss of muscle mass and/or its progressive weakening and degeneration. "Muscle wasting" refers to the progressive loss of muscle mass and/or to the progressive weakening and degeneration of muscles, including the skeletal or voluntary muscles which control movement, cardiac muscles which control the heart, and smooth muscles.

The loss of muscle mass that occurs during muscle wasting can be characterized by muscle protein catabolism. Protein catabolism occurs because of an abnormally high rate of protein degradation, an abnormally low rate of protein synthesis or a combination of both. Protein catabolism or depletion, whether the result of a high degree of protein degradation or of a low degree of protein synthesis, leads to a decrease in muscle mass and to muscle wasting. The term "catabolism" as is known in the art, means an energy burning form of metabolism.

In one embodiment, compositions of the instant invention are used to treat muscle wasting in patients with COPD. The methods of the instant invention promote increased muscle mass, muscle performance, muscle strength, or any combination thereof. Compositions of the invention may be administered to patients with COPD in combination with a resistance training regimen in order to gain cumulative benefits on muscle mass and/or performance.

In another embodiment, compositions of the instant invention are used to treat wasting in patients with COPD, wherein the wasting is characterized by involuntary loss of total body weight. Testosterone supplementation has been demonstrated to be effective in achieving weight gain in patients with COPD. Compositions comprising an antiestrogen may be administered to patients with COPD as an alternative to testosterone in order to promote weight gain in these patients while reducing side effects of testosterone therapy. Preferably, the antiestrogen is trans-clomiphene.

The compositions of the present invention may also be used to treat hypogonadism in hypogonadal males with COPD. Preferably the hypogonadism is secondary hypogonadism. Testosterone supplementation has been demonstrated to be effective in relieving symptoms associated with hypogonadism. Compositions comprising an antiestrogen may be used in hypogonadal patients with COPD as an alternative to testosterone therapy. Preferably, the antiestrogen is trans-clomiphene. Trans-clomiphene treatment has low liver and kidney toxicity and favorable effects on cholesterol, lipids and lymphocyte levels. Moreover, treatment with trans-clomiphene may have reduced side effects compared to testosterone therapy, such as PSA and cardiovascular risks.

Patients with COPD are often prescribed glucocorticosteriods, in inhalable form, in order to alleviate some of the symptoms of COPD. However, glucocorticosteriods have been demonstrated to reduce serum testosterone, and therefore aggravate hypogonadism in COPD patients. Compositions of the instant invention may be administered in conjunction with glucocorticosteroids in order to alleviate the tendency of glucocorticosteroids to promote hypogonadism in patients with COPD.

The terms "treat" or "treatment" as used in the instant application, refer to both therapeutic treatment and prophylactic or preventative measures, wherein the object is to prevent or slow down (lessen) an undesired physiological or psychological change or disorder, such as symptoms associated with COPD or the treatment thereof. For purposes of the present invention, beneficial or desired clinical results include, but are not limited to, alleviation of symptoms, diminishment of extent of disease, stabilized (i.e., not worsening) state of disease, delay or slowing of disease progression, amelioration or palliation of the disease state and remission (whether partial or total), whether detectable or undetectable. "Treatment" can also mean prolonging survival as compared to expected survival if not receiving treatment. Individuals in need of treatment include those already with the condition or disorder as well as those prone to develop the condition or disorder or those in whom the condition or disorder is to be prevented.

The terms "modulate" or "modulating", as used in the instant application, refer to both therapeutic treatment and prophylactic or preventative measures, wherein the object is to prevent or slow down (lessen) an undesired clinical parameter. For purposes of the present invention, beneficial or desired clinical results include, but are not limited to, correcting of clinical parameter, diminishment of extent of clinical parameter, stabilized (i.e., not worsening) clinical parameter and delay or slowing of extent of clinical parameter.

By "antiestrogen" it is meant a compound that prevents estrogens from expressing their effects on estrogen dependent target tissues consequently antagonizing a variety of estrogen-dependent processes. Based on the unexpected finding that the antiestrogenic trans-clomiphene isomer elevates tesostosterone levels to a greater degree than mixtures of trans- and cis-clomiphene, it is expected that compounds with antiestrogenic activity will be useful in treating psychological distress. In all cases, antiestrogens useful in the practice of the instant invention are those capable of elevating testosterone levels in a mammal. Without wishing to be bound by theory, it is believed that administration of antiestrogens will result in elevated testosterone levels by blocking the negative feedback exerted by normal estrogens on the pituitary leading to increases in LH and FSH. In men, these increased levels of gonadotropins stimulate the Leydig cells of the testes and result in the production of higher testosterone levels.

Antiestrogens useful in the practice of the instant invention may be pure antiestrogens or may have partial estrogenic action as in the case of the selective estrogen receptor modulators (SERMs) which exhibit antiestrogenic properties in some tissues and estrogenic tissues in others.

Pure antiestrogens of the invention include, without limitation: RU 58,688, described in Van de Velde et al., Ann. NY Acad. Sci., 761(3):164-175 (1995); 13-methyl-7-[9-(4,4,5,5,5-pentafluoropentylsulfinyl)nonyl]-7,8,9,11,12,13,14,15,16,17-decahydro-6H-cyclopenta[a]-phenanthrene-3,17-diol (ICI 182,780/fulvestrant) and other compounds described in EP 0138504; N-butyl-11-[(7R,8S,9S,13S,14S,17S)-3,17-dihydroxy-13-methyl-6,7,8,9,11,12,14,15,16,17-decahydro-cyclopena[a]phenanthren-7-yl]-N-methyl-undecanamide (ICI 164,384), described in Wakeling and Bowler, J. Endocrin., 112:R7-R110 (1987); (#)-7-pivaloyloxy-3-(4'pivaloyloxyphenyl)-4-methyl-2-(4''-(2''piperidinoethoxy)phenyl)-2H-benzopyran (EM-800/SCH 57050) and other compounds described in WO 96/26201; (2S)-3-(4-hydroxyphenyl)-4-methyl-2-[4-[2-(1-piperidyl)ethoxy]phenyl]-2H-chromen-7-ol (EM-652/SCH 57068) and the like.

SERMs of the invention include, without limitation, triphenylalkylenes such as triphenylethylenes, which include: 2-[4-(1,2-diphenylbut-1-enyl)phenoxy]-N,N-dimethyl-ethanamine (tamoxifen) and other compounds described in U.S. Pat. No. 4,536,516, incorporated herein by reference; Trans-4-(1-(4-(2-dimethylamino)ethoxy)phenyl)-2-phenyl-1-butenyl)phenol (4-hydroxytamoxifen) and other compounds described in U.S. Pat. No. 4,623,660, incorporated herein by reference; 1-[4'-dimethylaminoethoxy)phenyl]-1-(3'-hydroxyphenyl)-2-phenylbut-1-ene (droloxifene) and other compounds described in U.S. Pat. No. 5,047,431, incorporated herein by reference; 2-[p-[(Z)-4-chloro-1,2-diphenyl-1-butenyl]phenoxy]-N,N-dimethylethylamine (toremifene) and other compounds described in U.S. Pat. Nos. 4,696,949, 5,491,173 and 4,996,225, each of which is incorporated herein by reference; (E)-1-(2-(4-(1-(4-iodo-phenyl)-2-phenyl-but-1-enyl)-phenoxy)-ethyl)-pyrrolidinone (idoxifene) and other compounds described in U.S. Pat. No. 4,839,155, incorporated herein by reference; clomiphene and both its isomers; and compounds described in U.S. Pat. Nos. 4,696,949 and 5,491,173 and 6,576,645, each of which is incorporated herein by reference.

SERMS of the invention also include, without limitation, benzothiphene derivatives such as: [6-hydroxy-2-(4-hydroxyphenyl)-benzothiophen-3-yl]-[4-[2-(1-piperidinyl)ethoxy)phenyl]-methanone (raloxifene) and other compounds described in U.S. Pat. Nos. 4,418,068 and 5,393,763, both of which are incorporated herein by reference; LY353381; and LY335563 and other compounds described in WO 98/45286, WO 98/45287 and WO 98/45288; benzopyran derivatives such as: (#)-7-pivaloyloxy-3-(4'pivaloyloxyphenyl)-4-methyl-2-(4"-(2"piperidinoethoxy)phenyl)-2H-benzopyran (EM 800/SCH 57050) and other compounds described in WO 96/26201; (2S)-3-(4-hydroxyphenyl)-4-methyl-2-[4-[2-(1-piperidyl)ethoxy]phenyl]-2H-chromen-7-ol (EM 652); naphthalene derivatives such as: Cis-6-phenyl-5-[4-(2-pyrrolidin-1-yl-ethoxy)-phenyl]-5,6,7,8-tetrahydronaphthalen-2-ol (lasofoxifene/CP 336,156) and other compounds described in U.S. Pat. No. 5,552,412; 3,4-dihydro-2-(p-methoxyphenyl)-1-naphthyl-p-[2-(1-pyrrolidinyl)ethoxy]phenyl ketone (trioxifene/LY133314) and other compounds described in U.S. Pat. No. 4,230,862, incorporated herein by reference; and 1-(4-Substituted alkoxy)benzyl)naphthalene compounds such as those described in U.S. Pat. No. 6,509,356, incorporated herein by reference; chromans such as 3,4-trans-2,2-dimethyl-3-phenyl-4-[4-(2-(2-(pyrrolidin-1-yl)ethoxy)phenyl]-7-methoxychroman (levormeloxifene) and other compounds described in WO 97/25034, WO 97/25035, WO 97/25037 and WO 97/25038; and 1-(2-((4-(-methoxy-2,2,dimethyl-3-phenyl-chroman-4-yl)-phenoxy)-ethyl)-pyrrolidine (centchroman) and other compounds described in U.S. Pat. No. 3,822,287, incorporated herein by reference.

Other SERMs of the invention include, without limitation, the compounds described in U.S. Pat. Nos. 6,387,920, 6,743,815, 6,750,213, 6,869,969, 6,927,224, 7,045,540, 7,138,426, 7,151,196, and 7,157,604, each of which is incorporated herein by reference.

Further non-limiting antiestrogens of the invention include: 6α-chloro-16α-methyl-pregn-4-ene-3,20-dione (clometherone); 6-chloro-17-hydroxypregna-1,4,6-triene-3,20-dione (delmadinone); 1-[2-[4-[1-(4-methoxyphenyl)-2-nitro-2-phenylethenyl]phenoxy]ethyl]-pyrrolidine (nitromifene/CN-55,945-27); and 1-[2-[p-(3,4-Dihydro-6-methoxy-2-phenyl-1-naphthyl)phenoxy]ethyl]pyrrolidine (nafoxidene).

Further non-limiting antiestrogens of the invention include indoles such as those disclosed in J. Med. Chem., 33:2635-2640 (1990), J. Med. Chem., 30:131-136 (1987), WO 93/10741, WO 95/17383, WO 93/23374 and U.S. Pat. Nos. 6,503,938 and 6,069,153, both of which are incorporated herein by reference.

Further non-limiting antiestrogens of the invention include 2-[3-(1-cyano-1-methyl-ethyl)-5-(1H-1,2,4-triazol-1-ylmethyl)phenyl]-2-methyl-propanenitrile (anastrozole) and other compounds described in EP 0296749; 6-Methylenandrosta-1,4-diene-3,17-dione (exemestane) and other compounds described in U.S. Pat. No. 4,808,616, incorporated herein by reference; 4-[(4-cyanophenyl)-(1,2,4-triazol-1-yl)methyl]benzonitrile (letrozole) and other compounds described in U.S. Pat. No. 5,473,078, incorporated herein by reference; 1-[4'-dimethylaminoethoxy)phenyl]-1-(3'-hydroxyphenyl)-2-phenylbut-1-ene (droloxifene) and other compounds described in U.S. Pat. No. 5,047,431, incorporated herein by reference; 2α,3α-Epithio-5α-androstan-17β-ol (epitiostanol); 2α,3α-Epitio-5α-androstane-17β-yl-1-methoxycyclopentyloxy (mepitiostane); 4-[(2Z,4Z)-4-(4-hydroxyphenyl)hexa-2,4-dien-3-yl]phenol (cycladiene) and other compounds described in U.S. Pat. Nos. 2,464,203 and 2,465,505, both of which are incorporated herein by reference; CI-680 described in Unlisted Drugs, 28(10): 169(O) (1976); CI-628 described in Unlisted Drugs, 26(7): 106(1) (1974); 13-ethyl-17α-ethynl-17β-hydroxygona-4,9,1-trien-3-one (R2323); diphenol hydrochrysene and erythyro-MEA both described in Geynet, et al., Gynecol. Invest. 3(1):2-29 (1972); 1-[1-chloro-2,2-bis(4-methoxyphenyl)ethenyl]-4-methoxy-benzene (chlorotrianisene) described in Merck Index, $10^{th}$ ed., #2149; 1-[4-(2-Diethylaminoethoxy)phenyl]-1-phenyl-2-(p-anisyl)ethanol (ethamoxytriphetol) described in Merck Index, $10^{th}$ ed., #3668; and 2-p-Chlorophenyl-1-[p-(2-diethylaminoethoxy)phenyl]-1-p-tolylethanol (triparanol) and other compounds described in U.S. Pat. No. 2,914,562, incorporated herein by reference.

Still other antiestrogens of the invention include, without limitation: (2e)-3-(4-((1e)-1,2-diphenylbut-1-enyl)phenyl) acrylic acid (GW5638), GW7604 and other compounds described in Wilson et al., Endocrinology, 138(9):3901-3911 (1997) and WO 95/10513; 1-[4-(2-diethylaminoethoxy)phenyl]-2-(4-methoxyphenyl)-1-phenyl-ethanol (MER-25), N,N-diethyl-2-[4-(5-methoxy-2-phenyl-3H-inden-1-yl)phenoxy]ethanamine hydrochloride (U-11,555A), 1-[2-[4-(6-methoxy-2-phenyl-3,4-dihydronaphthalen-1-yl)phenoxy]ethyl]pyrrolidine hydrochloride (U-11,100A), ICI-46,669, 2-[4-[(Z)-1,2-diphenylbut-1-enyl]phenoxy]-N,N-dimethyl-ethanamine; 2-hydroxypropane-1,2,3-tricarboxylic acid (ICI-46,474) and other compounds described in Terenius et al., Gynec. Invest., 3:96-107 (1972); 2-Hydroxy-6-naphthalenepropionic acid (allenolic acid); [4-[(4-acetyloxyphenyl)-cyclohexylidene-methyl]phenyl]acetate (cyclofenyl/ICI-48213); [6-hydroxy-2-(4-hydroxyphenyl)benzothiophen-3-yl]-[4-[2-(1-piperidyl)ethoxy]phenyl]methanone (keoxifene); 4-[(Z)-1-[4-(2-dimethylaminoethoxy)phenyl]-2-(4-propan-2-ylphenyl)but-1-enyl]phenol (DP-TAT-59/miproxifene); (1RS,2RS)-4,4'-diacetoxy-5,5'-difluoro-(1-ethyl-2-methylene)di-m-phenylenediacetate (acefluranol); 6-hydroxy-2-(p-hydroxyphenyl)-benzo(b)thien-3-yl[2-(1-pyrrolidinyl)-ethoxyphenyl]ketone (LY-117018); and [6-hydroxy-2-(4-hydroxy-phenyl)benzo(b)thien-3-yl]-[4-(2-(1-piperdinyl)-ethoxy)phenyl]methanone (LY-156758).

Still other antiestrogens of the invention include, without limitation: non-steroidal estrogen receptor ligands such as those described in U.S. Pat. Nos. 5,681,835, 5,877,219, 6,207,716, 6,340,774 and 6,599,921, each of which is incorporated herein by reference; steroid derivatives such as those described in U.S. Pat. No. 4,659,516, incorporated herein by reference; 7α-11-aminoalkyl-estratrienes such as those described in WO 98/07740; 11-β-halogen-7α-substituted estratrienes such as those described in WO 99/33855; 17α-alkyl-17β-oxy-estratrienes such as those described in U.S. patent application Ser. No. 10/305,418, incorporated herein by reference; 2-phenyl-1-[4-(2-aminoethoxy)-benzyl]-indoles such as those described in U.S. Pat. No. 7,132,417, incorporated herein by reference; 4-fluoroalkyl-2h-benzopryans such as those described in U.S. Pat. No. 6,844,336, incorporated herein by reference; (4-(2-(2-aza-bicyclo[2.2.1]hept-2-yl)-ethoxy)-phenyl)-(6-hydroxy-2-(4-hydroxy-phenyl)-benzo[b]thiophen-3-yl)-methanone and other benzothiophenes described in WO 95/10513 and U.S. Pat. No. 4,133,814, incorporated herein by reference; 2-phenyl-1-[4-(2-aminoethoxy)-benzyl]-indoles such as those described in U.S. Pat. No. 5,998,402, incorporated herein by reference; 3-[4-(2-Phenyl-Indole-1-ylmethyl)Phenyl]-Acrylamides and other compounds described in U.S. Pat. No. 5,985,910, incorporated herein by reference; 2-phenyl-1-[4-(amino-1-yl-alk-1-ynyl)-benzyl]-1H-indol-5-ols and other compounds described in U.S. Pat. Nos. 5,780,497 and 5,880,137, both of which are incorporated herein by reference; steroids such as those described in U.S. Pat. Nos. 6,455,517, 6,548,491, 6,747,018 and 7,041,839, each of which is incorporated herein by reference; Di-(3'-hydroxyphenyl)-alkane compounds such as those described in U.S. Pat. No. 4,094,994, incorporated herein by reference; phenol derivatives such as those described in U.S. Pat. No. 4,751,240, incorporated herein by reference; 2,3-diaryl-2H-1-benzopyran analogs such as those described in Saeed et al., J. Med. Chem., 33:3210-3216 (1990) and Sharma et al., J. Med. Chem. 33:3216-3229 (1990); and benzofuran and triarylfuran analogs such as those described in Durani et al., J. Med. Chem., 32:1700-1707 (1989).

Suitable pharmaceutical compositions or unit dosage form may be in the form of solids, such as tablets or filled capsules or liquids such as solutions, suspensions, emulsions, elixirs or capsules filled with the same, all for oral use. The compositions may also be in the form of sterile injectable solutions or emulsions for parenteral (including subcutaneous) use. Such pharmaceutical compositions and unit dosage forms thereof may comprise ingredients in conventional proportions.

Compositions according to the present invention may be administered by any route of administration including, but not limited to, oral, aural, intravenous, subcutaneous, buccal, transmucosal, intrathecal, intradermal, intracisternal, intramuscular, transdermal, intraperitoneal, epidural, vaginal, rectal, intranasal, sublingual, intra-articular, intra-cerebrospinal and intrasynovial.

Compositions according to the present invention may comprise trans-clomiphene at a dosage between one mg to about 200 mg (although the determination of optimal dosages is with the level of ordinary skill in the art). The composition may comprise trans-clomiphene at a dosage of about 1 mg, 2 mg, 3, mg, 4 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg or there between. The composition may also comprise trans-clomiphene and cis-clomiphene at a ratio of about 71/29, 72/28, 73/27, 74/26, 75/25, 76/24, 77/23, 78/22, 79/21, 80/20, 81/19, 82/18, 83/17, 84/16, 85/15, 86/14, 87/13, 88/12, 89/11, 90/10, 91/9, 92/8, 93/7, 94/6, 95/5, 96/4, 97/3, 98/2, 99/1, 99.5/0.5 or there between. Analogs of the trans- and cis-isomers of clomiphene such as those described in Ernst, et al. supra are also useful in the practice of the present invention.

Dosages are preferably (but not necessarily) administered as part of a dosage regimen designed to give rise to serum testosterone levels that mimic or correspond to the normal secretary total serum testosterone profile described in FIG. 1. For example, according to FIG. 1 a dosage of the preferred composition may be administered in a pharmaceutical formulation that would give rise to peak serum testosterone levels at around 8 a.m. Such pharmaceutical formulations may be in the form of sustained release formulations prepared as described for example in U.S. Pat. No. 6,221,399, Japanese patent 4-312522, Meshali et al, Int. J. Phar. 89:177-181 (1993), Kharenko et al, Intern. Symp. Control Rel. Bioact. Mater. 22:232-233 (1995), WO 95/35093, Dangprasit et al., Drug. Devel. and Incl. Pharm. 21 (20):2323-2337 (1995); U.S. Pat. Nos. 6,143,353, 6,190,591, 6,096,338, 6,129,933, 6,126,969, 6,248,363 and other sustained release formulations well known in the art.

Compositions of the present invention may also be administered in fast-release formulations, slow-release formulations or mixtures of fast-release and slow-release formulations such as a multi-layer tablet comprising at least one fast-release layer and at least one slow-release layer.

All of the references discussed herein are incorporated by reference in their entirety.

The following Examples are meant to be illustrative of the invention and is not intended to limit the scope of the invention as set out in the appended claims.

EXAMPLE 1

Effects of Clomids on Serum Testosterone and Cholesterol in Male Baboons

Adult, male, Baboons were given 1.5 mg/kg of Clomid, Enclomid (trans-Clomid) or Zuclomid (cis-Clomid) for 12 consecutive days. The samples analyzed were sera taken on the day of first treatment before being given test article (day 0), after 12 days of treatment (day 12) and 7 days after the last treatment (end or wash-out).

1. Effects on Body Weight and Serum LH, FSH, PRL and Testosterone

Figure 3:
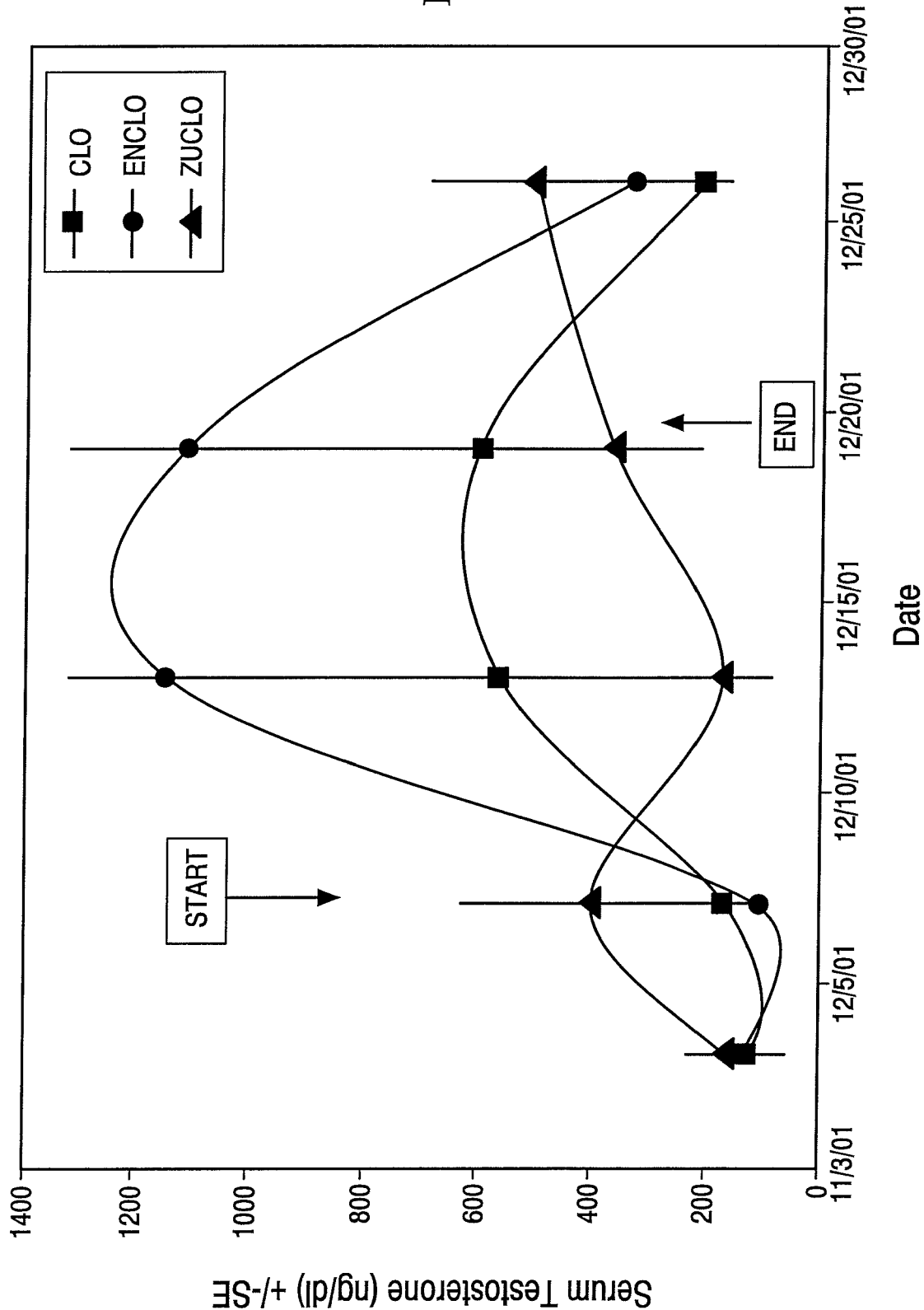
FIG. 3 is a graphic demonstration of the time course of serum testosterone levels with Clomid (clomiphene), Enclomid (trans-clomiphene) and Zuclomid (cis-clomiphene).
Figure 4:
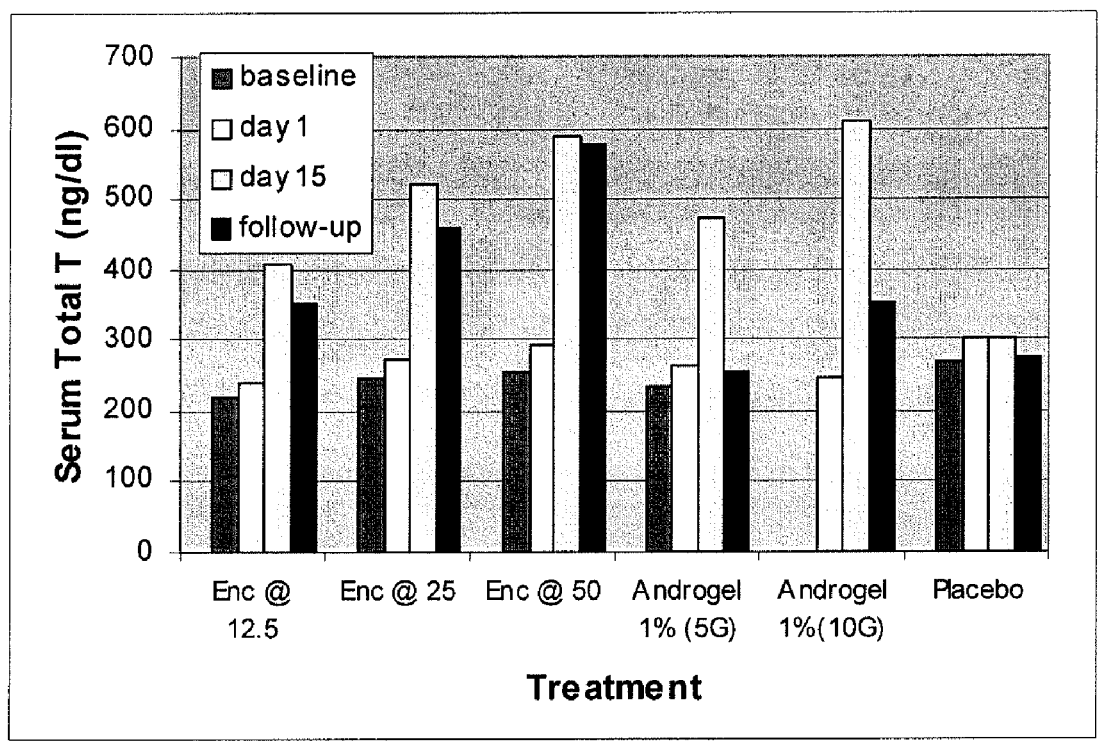
FIG. 4 demonstrates the effect of Androxal™ or Androgel® on testosterone levels.

There were significant increases in total serum testosterone in the group receiving Enclomid. See Table 1. There were no differences among groups in the baseline period or at day 0. There were also no differences among the three groups 7 days after treatment (the washout period). However, Enclomid produced higher levels of testosterone compared to Clomid and Zuclomid on day 6 ($p=0.03$ and $p=0.00002$ respectively) and compared to Zuclomid on day 12 ($p=0.047$). Zuclomid clearly did not raise total serum testosterone to any extent. Compared to the animals receiving Enclomid, the animals receiving Clomid exhibited more variable total testosterone levels on day 6 and later as judged by their coefficients of variations. When we looked at the time course of the effects (FIG. 3), we determined that only Enclomid significantly and statistically raised total serum testosterone on days 6 and 12 compared with either baseline or day 0 values. Moreover, cessation of Enclomid treatment, resulted in a significant drop in the level of total serum testosterone between day 12 and day 18 (washout). This indicates that Enclomid is readily cleared from the circulation consistent with the metabolic clearance seen for Enclomid in humans. Enclomid was clearly better and more consistent than Clomid itself and Zuclomid was ineffective.

TABLE 1

| | | Serum Testosterone Levels (ng/dl) | | | | |
|---|---|---|---|---|---|---|
| Group | ID | baseline Dec. 3, 2001 | 0 day Dec. 7, 2001 | 6 days Dec. 13, 2001 | 12 days Dec. 20, 2001 | wash-out Dec. 26, 2001 |
| CLO | 7500 | 79.01 | 76.15 | 940.97 | 891.5 | 150.9 |
| | 9012 | 97.55 | 305.24 | 585.92 | 555.6 | 316.3 |
| | 9097 | 158.06 | 102.94 | 151.12 | 318.9 | 143.6 |
| | mean | 111.5 | 161.4 | 559.3 | 588.7 | 203.6 |
| | SD | 41.3 | 125.2 | 395.6 | 287.7 | 97.7 |
| ENCLO | 7223 | 64.57 | 74.96 | 1223.8 | 633.6 | 307.2 |
| | 8021 | 166.86 | 133.59 | 1128.2 | 1466 | 399.2 |
| | 8369 | 170.45 | 106.47 | 1081.1 | 1166 | 271 |

TABLE 1-continued

Serum Testosterone Levels (ng/dl)

| Group | ID | baseline Dec. 3, 2001 | 0 day Dec. 7, 2001 | 6 days Dec. 13, 2001 | 12 days Dec. 20, 2001 | wash-out Dec. 26, 2001 |
|---|---|---|---|---|---|---|
| | mean | 134.0 | 105.0 | 1144.4 | 1088.5 | 325.8 |
| | SD | 60.1 | 29.3 | 72.7 | 421.6 | 66.1 |
| ZUCLO | 7438 | 124.84 | 210.4 | 137.51 | 314.5 | 359.7 |
| | 8292 | 104.66 | 67.37 | 169.98 | 406.1 | 860.5 |
| | 10098 | 282.29 | 904.82 | 227.95 | 353.0 | 274.1 |
| | mean | 170.6 | 394.2 | 178.5 | 357.9 | 498.1 |
| | SD | 97.3 | 448.0 | 45.8 | 46.0 | 316.8 |
| | ANOVA | p = 0.61 | p = 0.43 | p = 0.007 | p = 0.57 | p = 0.256 |
| | K-W | p = 0.56 | p = 0.84 | p = 0.051 | p = 0.079 | p = 0.252 |

There were no changes in serum LH or FSH. The ratio of total serum testosterone to LH followed the same pattern as total serum testosterone, suggesting a lack of dependence (data not shown). There was also no change in body weight during the 12 day study. There was a decrease in serum prolactin (PRL) during the study in the group receiving Enclomid, suggesting an effect of antiestrogen that has been described in part (Ben-Jonathan and Hnasko, 2001) and expected on the basis of the fact that as men age, testosterone declines and Prolactin increase (Feldman et al., 2002).

2. Effects on Cholesterol Levels

Treatment with Enclomid tended to decrease serum cholesterol and Zuclomid tended to increase the same parameter. Preliminary analysis indicated that the changes in cholesterol levels were not statistically significant and that the changes were within the normal range. Due to the observed trend for the two isomers to demonstrate opposite effects on cholesterol levels over a short period of time, further analysis was conducted.

Detailed analysis indicated that Enclomid resulted in an 8% decrease in serum cholesterol levels. Conversely, treatment with Zuclomid resulted in a 22% increase in serum cholesterol levels. Treatment with Clomid resulted in a slight increase in serum cholesterol levels. The opposite effect of Enclomid and Zuclomid on serum cholesterol levels is not unexpected given that the isomers have, alternatively, estrogen agonist or antagonist activity. These results indicate that Enclomid may be used for treating patients with high cholesterol levels. These results also indicate that Enclomid may be more benign than Zuclomid with respect to serum cholesterol if used chronically for increasing testosterone levels.

3. Effects on Clinical Chemistry Parameters

The mean values for each parameter did not differ among the three groups for any test parameter at the beginning of the study as determined by ANOVA or by the Kruskal-Wallis test. All groups exhibited normal values at each parameter except for (1) serum sodium; a related calculated parameter, anionic gap, which were low for all nine baboons throughout the trial; (2) serum glucose; and (3) BUN which were high on day 0 for the group which would be treated with Enclomid. On day 12 of treatment and 7 days after treatment (washout), there were no differences among groups for any parameter except anionic gap that showed that the Clomid and Zuclomid groups had lower values than the Enclomid group. The values of serum sodium and anionic gap appear to be anomalies associated with this group of baboons.

There were substantive effects on the red blood cell population with Enclomid and Zuclomid and on hematocrit with Zuclomid. All the compounds lower the mean cell hemoglobin concentration (MCHC) either at day 0 or at the endpoint. With no change in mean cell hemoglobin (MCH) and an increase in the mean cell volume (MCV), the lowering of MCHC is predictable. Although testosterone might be expected to raise hematocrit, only Zuclomid treatment, which did not increase total serum testosterone, demonstrated a statistical difference. Clearly, men in a clinical trial that uses Zuclomid should be monitored for the characteristics of their red blood cell population. Enclomid would be predicted to have less of an effect.

There appears to be a clear effect of 12-day Enclomid treatment on platelets although the values found stayed within the normal range. One thing to consider here is the sexual dimorphism in platelet counts between male and female baboons (279 for males vs. 348 for females). This is likely to be due to hormones. Since the Enclomid group demonstrated increased testosterone, the lowering of the platelet count could be secondary to the change in testosterone in this group. Moreover, treatment with Enclomid pushed the platelet count to its normal male level from a day 0 level that was the high end of the normal range for this group. Enclomid would not necessarily predict a deleterious effect on platelets.

All the Clomids tested had effects on the white blood cell (WBC) population, the most striking was that of Enclomid on raising the counts of lymphocytes and eosinophiles. The effects are not as straightforward as they would seem to be. There appears to be a strong effect of Enclonud on lowering the per cent of granulocytes in the blood. The effects are very strong after the 7-day washout period when the values are decreased below the normal range. (This time course could reflect the relatively long time required to affect change the WBC population.) There is little sexual dimorphism in baboons with respect to the white blood cell populations, so the effects are more likely to be due to the compound itself than changes in testosterone. However, when we look at the calculated count of granulocytes using the WBC count, we find no differences in granulocyte count due to any compound. Concomitantly, it is the lymphocyte story that is the most interesting. Both the count and per cent lymphocytes in the population increase with Enclomid treatment. Whereas the mean values of per cent lymphocytes remain in the normal range, given the trend for an increase in WBC count, the net effect is an increase in lymphocyte count with Enclomid. This eosinophil result is analogous. There is a clear implication for treating men who have low lymphocytes, such as men who are HIV-positive. Since Enclomid is unlikely to lower lymphocytes based on this result, a case could be made for its use in the population of men with AIDS. These individuals are often treated with agents that are intended to raise testosterone due to the wasting effects of disease. Low liver and kidney toxicity and favorable effects on cholesterol and lipids are also highly favored attributes for any medication intended for use HIV-positive men who are already compromised by their disease.

The increase in serum glucose with Clomid or Zuclomid was within the normal range. In the case of Enclomid where the mean serum glucose values were high on day 0, there were no increases with treatment. There was no evidence that Enclomid would have a deleterious effect on blood glucose.

No clearly adverse effects on liver function are apparent as judged by the enzymes AST and ALT. The trend in these values was a decrease with treatment. An increase in the level of enzymes in the serum would indicate liver damage. ALT/SGPT was out of range low at the end of the study for the Clomid group although the differences over the treatment period were not statistically significant. The changes with Enclomid and Zuclomid were within the normal range. AST is depressed in pregnancy; thus the action of an estrogen agonist such as Zuclomid in lowering the marginal AST level could be rationalized. Alkaline phosphatase (ALP) is also found in the liver and is elevated various disease states. The lowering of ALP argues further against hepatic damage. There were no changes in serum albumin, also a liver product. A strong suppression of serum albumin over an extended time period could contribute to free serum steroid hormone levels in humans although a more important role is played by sex hormone binding globulin. As a bottom line, none of the compounds could be linked to liver damage on the basis of the parameters assayed.

Osteoblastic activity and diseases of the bone are accompanied by high serum ALP values. ALP was not elevated following Zuclomid treatment and was decreased in value following Enclomid treatment. The trends would predict a more benign result for the use of Enclomid compared to Zuclomid.

Although BUN and BUN/creatinine were altered during the study in the Clomid and Enclomid groups, the lack of a definitive change in creatinine argues against renal dysfunction. A loss of glomerular filtration capacity would result in an increase in BUN. Decreased BUN occurs in humans due to poor nutrition (not likely in a controlled setting), or high fluid intake (presumably accompanied by edema). Also, despite an increase in total serum testosterone between day 0 and Day 12 with Enclomid, there were no differences between serum creatinine values, arguing against an increase in muscle mass over this short time interval.

Serum sodium levels were lower than reference values for all animals throughout the study. Serum carbon dioxide was higher than reference values on day 12 for the Clomid and Zuclomid groups. Serum anion gap was lower for all animals throughout the study, paralleling the sodium results. Enclomid raised this parameter towards normal values. The electrolyte imbalances detected in the test animals throughout all treatment periods remains elusive but might be part of the same fluid derangement phenomenon suggested by the BUN results.

The foregoing results indicate that Enclomid is more effective than Clomid or Zuclomid at enhancing total serum testosterone. Zuclomid is clearly not effective and that deficiency limits any use of Clomid for hypogonadism, particularly since the Zuclomid component of Clomid would predominate in the circulation over time given its longer half-life.

The strong activity of Enclomid to increase serum testosterone levels lends itself for use in men with low total or free serum testosterone including, without limitation, ageing men, men undergoing renal dialysis, men with end-stage pulmonary failure, men on certain narcotics, male AIDS patients experiencing muscle loss and/or compromised T4 lymphocyte counts and especially men with COPD.

EXAMPLE 2

Treating Wasting in Patients with COPD

Prior to administration of trans-clomiphene, blood samples are taken from subject individuals and testosterone levels are measured using methodologies described for example in Matsumoto, et al. Clin. Endocrinol. Metab. 56; 720 (1983) (incorporated herein by reference). Sex hormone binding globulin (SHBG), both free and bound to testosterone, may also be measured as described for example in Tenover et al. J. Clin. Endocrinol. Metab. 65:1118 (1987) which describe measurement of SHBG by both a [$^3$H]dihydrotestosterone saturation analysis and by radioimmunoassay. Non-SHBG-bound testosterone levels (bioavailable testosterone) are also measured for example according to Tenover et al. J. Clin. Endocrinol and Metab. 65:1118 (1987). See also Soderguard et al. J. Steroid Biochem 16:801 (1982) incorporated herein by reference.

Patients are given daily dosages of 1.5 mg/kg clomiphene, wherein the ratio of trans-clomiphene to cis-clomiphene is greater than 71/29. Patients are monitored for testosterone levels and increases in muscle mass and/or weight gain such that the dosage amount and dosage frequency may be adjusted to achieve therapeutic levels of testosterone and improvements in muscle mass and/or weight gain in the patient.

EXAMPLE 3

Treating Secondary Hypogonadism in Males with COPD

Prior to administration of trans-clomiphene, blood samples are taken from subject males and testosterone levels are measured using methodologies described for example in Matsumoto, et al. Clin. Endocrinol. Metab. 56; 720 (1983) (incorporated herein by reference). Sex hormone binding globulin (SHBG), both free and bound to testosterone, may also be measured as described for example in Tenover et al. J. Clin. Endocrinol. Metab. 65:1118 (1987) which describe measurement of SHBG by both a [$^3$H] dihydrotestosterone saturation analysis and by radioimmunoassay. Non-SHBG-bound testosterone levels (bioavailable testosterone) are also measured for example according to Tenover et al. J. Clin. Endocrinol and Metab. 65:1118 (1987). See also Soderguard et al. J. Steroid Biochem 16:801 (1982) incorporated herein by reference.

Patients are given daily dosages of 1.5 mg/kg clomiphene, wherein the ratio of trans-clomiphene to cis-clomiphene is greater than 71/29. Patients are monitored for testosterone levels such that the dosage amount and dosage frequency may be adjusted to achieve therapeutic levels of testosterone in the COPD patient.

EXAMPLE 4

Comparison of Androxal™ to Androgel®

A placebo controlled challenge study was conducted at the Advanced Biological Research, Inc. (ABR) Clinical Research Center in Hackensack, N.J. to compare orally administered Androxal™ (trans-clomiphene) to Androgel® (testosterone) in hypogonadal men. Androgel® (Solvay Pharmaceuticals, Inc.) consists of a cream that administers exogenous testosterone in a transdermal matrix.

The study enrolled 62 hypogonadal men with testosterone levels less than 300 ng/dl (normal 298-1034 ng/dl) that were randomized into 6 different arms, three doses of Androxal™ (12.5 mg, 25 mg, and 50 mg), placebo, and both high and low doses of Androgel®. Half of the men in each of the Androxal™ and placebo arms were randomized into cohorts that underwent in-clinic sessions on days 1 and 14 to determine pharmacokinetic parameters for Androxal™ as well as cyclical changes in testosterone. The placebo and Androxal™ doses were administered in a double blind fashion. The Androgel® cream was administered in an open label fashion. Half of the Androgel® patients underwent in-clinic sessions similar to the other patients in the study. Following the two week drug exposure patients were followed for an additional seven to ten days to determine the status of their testosterone levels.

There were no side effects noted in either the Androxal™ or Androgel® arms of the study that were different than placebo. Furthermore, all doses produced statistically significant changes in testosterone from baseline testosterone levels. The low, mid and high doses of Androxal™ achieved mean increases of 169, 247, and 294 ng/dl respectively, while those of Androgel® 5 G, the lowest approved dose, and Androgel® 10 G, the highest approved dose, produced changes from baseline that were 212 and 363 ng/dl. These values were statistically indistinguishable from those changes achieved with Androxal™. This inability to show differences between Androxal™ and Androgel® appears to result from the highly variable results found when Androgel® is used. For example the 50 mg dose of Androxal™ raised mean total testosterone to 589±172 ng/dl after 15 days, a coefficient of variation (CV) of 29% and similar to the placebo group (36%). On the other hand Androgel® 5 G and 10 G yielded mean total testosterone values 473±289 ng/dl and 608±323 ng/dl, CV's of 61% and 53% respectively.

After 14 days of Androxal™ therapy all doses were associated with a total testosterone diurnal pattern similar to the placebo group, i.e. a morning peak, a mid-day trough and a rise overnight. Without being bound by theory, this pattern may be due to the mode of action of Androxal™, which appears to be mediated through effects on the hypothalamic-pituitary axis. The diurnal pattern for men on Androgel® was nearly flat. However, spikes in total testosterone for Androgel® were associated with dosing and often exceeded the normal high level of 1,034 ng/dl. Certain individuals on Androgel® 10 G were able to achieve peak levels of total testosterone of over 2500 ng/dl.

Figure 5:
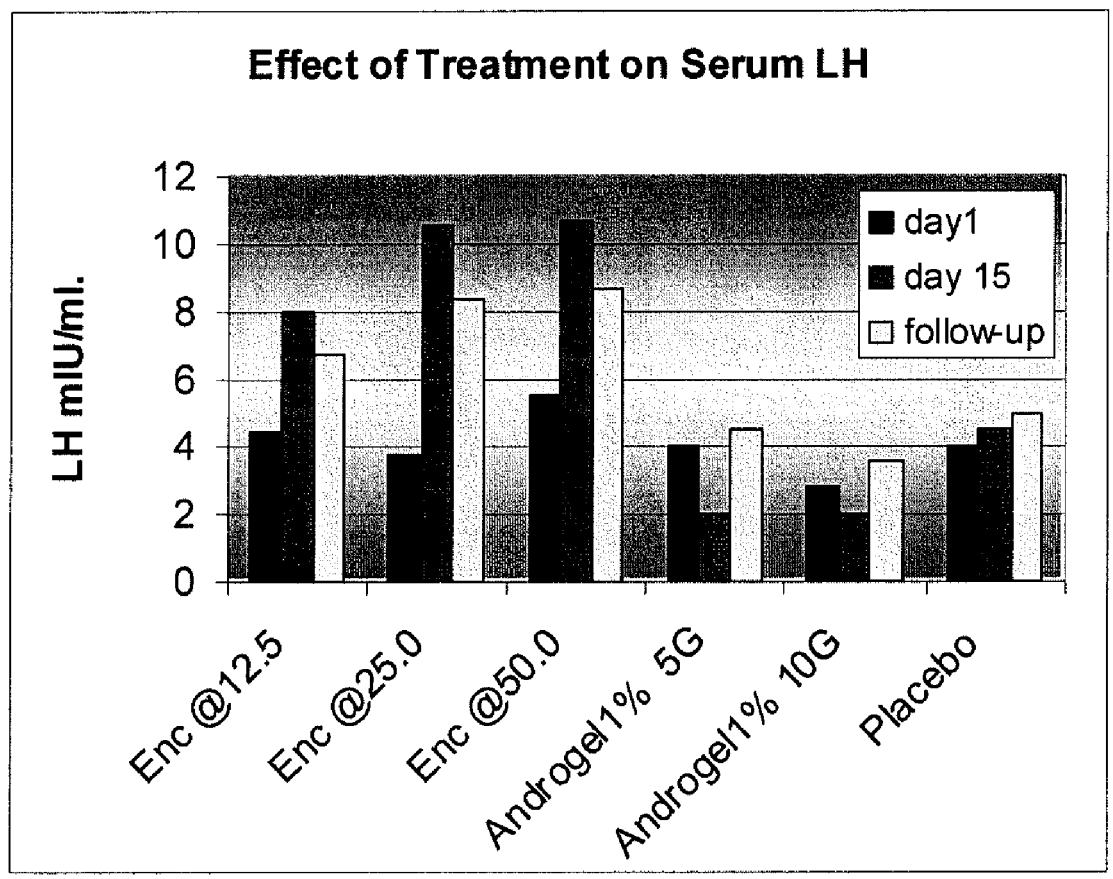
FIG. 5 demonstrates the effect of Androxal™ or Androgel® on LH levels

Treatment with Androxal™ produced a statistically significant increase in the serum levels of LH in the hypogonadal male subjects (FIG. 5). As in the case of total serum testosterone there was an unexpected continuation in the level of serum LH in the follow-up period (i.e., 7-10 days after cessation of daily oral treatment) where those levels remained high for the three doses of Androxal™. By comparison, treatment with AndroGel® initially decreased LH and after cessation there was an apparent rebound towards pre-treatment levels.

Figure 6:
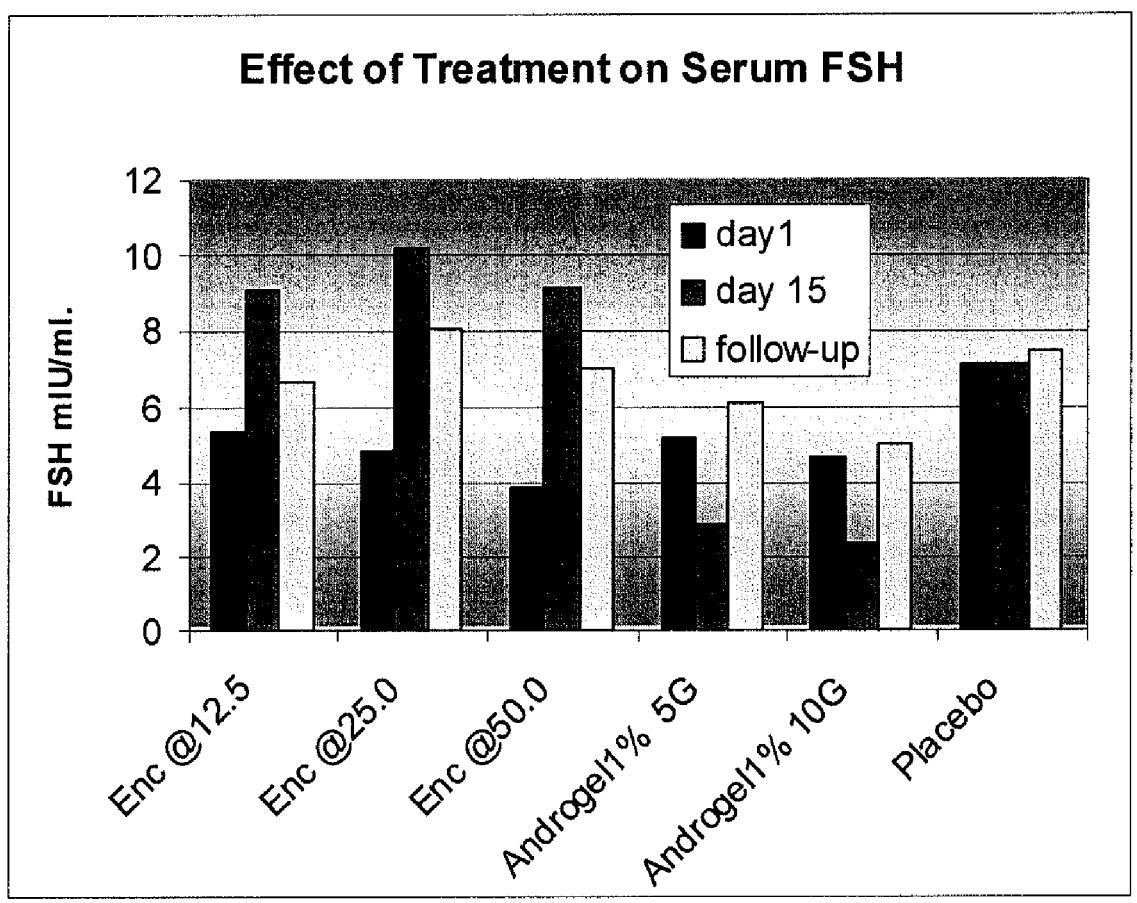
FIG. 6 demonstrates the effect of Androxal™ or Androgel® on FSH levels

Treatment with Androxal™ also produced a statistically significant increase in the serum levels of FSH in the hypogonadal male subjects (FIG. 6). The pattern of increasing FSH is similar to that seen in the case of LH, that is, all doses of Androxal™ boosts serum FSH which remains high during the follow-up period whereas AndroGel® suppresses the level of serum FSH and cessation of treatment allows serum FSH to rebound towards concentrations more similar to pre-treatment levels.

The effect on serum dihydroxytestosterone (DHT) levels were also measured. Men on Androxal™ experienced a favorable shift in their DHT to total testosterone. For example men on the 50 mg dose of Androxal™ experienced a DHT/TT ratio of 0.83 as compared to the placebo group ratio of 1.07. By contrast the DHT/TT ratio for either of the Androgel® groups was >1.5. The results indicate that men on Androgel® were gaining DHT faster than total testosterone. Thus the normal levels of DHT was disrupted relative to testosterone in men on Androgel® therapy.

Results of clinical chemistry parameters also indicated, unexpectedly, that men on Androxal™ experienced a non-dose dependent reduction in triglycerides. The reduction in triglycerides averaged a decrease of 19.1% after two weeks of therapy. This compared to a 5.9% reduction for the placebo group and increases of 0.3% and 22% for the Androgel® 5 G and 10 G respectively.

Based on this study we infer a number of potential advantages for Androxal™ as a potential therapy. First, Androxal™ appears to raise total testosterone into the normal range in a highly consistent manner without abnormally high spikes in serum testosterone. In addition, the use of trans-clomiphene to treat men that suffer secondary hypogonadism offers a new approach that potentially could offset one of the major side effects of exogenous therapies such as Androgel®. Exogenous therapies provide negative feedback thereby shutting down FSH and LH production. FSH is an essential reproductive hormone and in the male stimulates spermatogenesis. Long term exposure to exogenous testosterone, as a result of its effects on FSH production, causes a reduction in sperm synthesis, leading to the potential for transient infertility due to low sperm counts and therefore a resulting shrinkage of the testis, since the volume of the testis is related to the level of spermatogenesis within the seminiferus tubules. The increase in FSH levels also indicates that Androxal™ may be used to treat infertility in males, including hypogonadal males. Secondly, Androxal™ appears to improve the DHT/TT ratio, a potentially important consideration from the standpoint of prostate cancer. Thirdly, the maintenance of a normal diurnal pattern improves testosterone levels in a more natural fashion. Finally, the tendency to lower triglycerides may be an advantage to many men.

We claim:

1. A method for treating wasting in a hypogonadal male, comprising administering to the male a composition consisting essentially of trans-clomiphene or pharmaceutically acceptable salts thereof and optionally one or more pharmaceutically acceptable diluents, adjuvants, carriers or excipients in an effective amount to treat said wasting in the hypogonadal male.

2. The method of claim 1, wherein the composition is administered in a dosage of 1-200 mg of trans-clomiphene per day.

3. The method of claim 2, wherein the composition is administered in a dosage of 50 mg of trans-clomiphene per day.

4. The method of claim 1, wherein the composition is administered in a dosage of 1.5 mg/kg of trans-clomiphene per day.

5. The method of claim 1, wherein the composition consists essentially of 12.5 mg of trans-clomiphene or a pharmaceutically effective salt thereof.

6. The method of claim 1, wherein the composition is a capsule.

7. The method of claim 1, wherein the composition is a capsule.

* * * * *

UNITED STATES PATENT AND TRADEMARK OFFICE
CERTIFICATE OF CORRECTION

PATENT NO. : 7,737,185 B2
APPLICATION NO. : 11/750190
DATED : June 15, 2010
INVENTOR(S) : Joseph S. Podolski et al.

It is certified that error appears in the above-identified patent and that said Letters Patent is hereby corrected as shown below:

Delete the title page and substitute therefore with the attached title page showing the corrected number of claims in patent.

IN THE CLAIMS

At column 18, lines 61 and 62, please delete claim 7 in its entirety.

Signed and Sealed this
Eighth Day of April, 2014

Michelle K. Lee
*Deputy Director of the United States Patent and Trademark Office*

(12) United States Patent
Podolski et al.

(10) Patent No.: US 7,737,185 B2
(45) Date of Patent: Jun. 15, 2010

(54) **METHODS AND COMPOSITIONS WITH *TRANS*-CLOMIPHENE**

(75) Inventors: Joseph S. Podolski, The Woodlands, TX (US); Ronald Wiehle, Houston, TX (US)

(73) Assignee: Repros Therapeutics Inc., The Woodlands, TX (US)

( * ) Notice: Subject to any disclaimer, the term of this patent is extended or adjusted under 35 U.S.C. 154(b) by 253 days.

(21) Appl. No.: 11/750,190

(22) Filed: May 17, 2007

(65) Prior Publication Data

US 2007/0249726 A1 Oct. 25, 2007

Related U.S. Application Data

(63) Continuation-in-part of application No. 10/427,768, filed on Apr. 30, 2003, now Pat. No. 7,368,480, which is a continuation-in-part of application No. PCT/US02/21524, filed on Jul. 9, 2002.

(60) Provisional application No. 60/304,313, filed on Jul. 9, 2001.

(51) Int. Cl.
*A61K 31/135* (2006.01)
*A61P 11/00* (2006.01)

(52) U.S. Cl. ............................................. 514/651
(58) Field of Classification Search ............ None
See application file for complete search history.

(56) References Cited

U.S. PATENT DOCUMENTS

| | | | |
|---|---|---|---|
| 4,061,733 A | 12/1977 | Gunjikar | |
| 4,820,736 A | 4/1989 | Jensen et al. | |
| 4,894,373 A | 1/1990 | Young | |
| 5,728,688 A | 3/1998 | Labrie | |
| 5,861,389 A | 1/1999 | Radlmaier | |
| 6,017,964 A | 1/2000 | MacLean et al. | |
| 6,096,338 A | 8/2000 | Lacy | |
| 6,126,969 A | 10/2000 | Shah | |
| 6,129,933 A | 10/2000 | Oshlack | |
| 6,143,353 A | 11/2000 | Oshlack | |
| 6,190,591 B1 | 2/2001 | Van Lengerich | |
| 6,221,399 B1 | 4/2001 | Rolfes | |
| 6,248,363 B1 | 6/2001 | Patel | |
| 6,291,505 B1 | 9/2001 | Huebner et al. | |
| 6,342,250 B1 | 1/2002 | Masters | |
| 6,391,920 B1 | 5/2002 | Fisch | |
| 6,583,129 B1 | 6/2003 | Mazer et al. | |
| 6,600,010 B2 | 7/2003 | Mao et al. | |
| 6,638,528 B1 | 10/2003 | Kanios | |
| 6,645,974 B2 | 11/2003 | Hutchinson et al. | |
| 6,653,297 B1 | 11/2003 | Hodgen | |
| 6,685,957 B1 | 2/2004 | Bezemer et al. | |
| 6,743,448 B2 | 6/2004 | Kryger | |
| 7,105,679 B2 | 9/2006 | Kanojia et al. | |
| 2002/0120012 A1 | 8/2002 | Fisch | |
| 2002/0183296 A1 | 12/2002 | Dudley et al. | |
| 2004/0097597 A1 | 5/2004 | Podolski et al. | |
| 2004/0171697 A1 | 9/2004 | Podolski et al. | |
| 2004/0220154 A1 | 11/2004 | Kryger | |
| 2004/0241224 A1 | 12/2004 | Podolski et al. | |
| 2006/0269611 A1 | 11/2006 | Steiner et al. | |

FOREIGN PATENT DOCUMENTS

| | | |
|---|---|---|
| AU | 2001261684 | 12/2001 |
| EP | 0206021 A | 8/1988 |
| EP | 0430388 A2 | 6/1991 |
| EP | 0888775 A2 | 7/1999 |
| EP | 1829534 A1 | 3/2006 |
| JP | 4-312522 | 11/1992 |
| WO | WO 95/35093 | 12/1995 |
| WO | WO 01/34117 A1 | 5/2001 |
| WO | WO 01/91744 A1 | 12/2001 |
| WO | WO 03/005954 A2 | 1/2003 |
| WO | WO 03/005954 A3 | 1/2003 |
| WO | WO 03/026568 A2 | 4/2003 |
| WO | WO 03/072092 | 9/2003 |
| WO | WO 2006/019916 | 2/2006 |
| WO | WO 2006/084153 | 8/2006 |
| WO | WO 2006/102232 | 9/2006 |
| WO | WO 2007/019165 | 2/2007 |
| WO | WO 2009/051908 | 4/2009 |

OTHER PUBLICATIONS

Laghi et al. (Am J Respir Crit Care, Med vol. 171, pp. 598-605, 2005).*
Debigare et al. (Am. J. Respir. Crit. Care Med., vol. 165, No. 9, 2001, pp. 1712-1717).*
Casaburi et al. (Am J Respir Crit Care Med. vol. 170, pp. 870-878, 2004).*
Banner A. S. (Lancet, vol. 354, Aug. 7, 1999, pp. 440-441).*
Vippagunta (Adv. Drug Del. Rev., 2001, vol. 48, 2001. pp. 3-26.*
ACCE Clinical Practice Guidelines for the Evaluation and Treatment of Hypogonadism in Adult Male Patients (1996).

(Continued)

*Primary Examiner*—Brian-Yong S Kwon
(74) *Attorney, Agent, or Firm*—Howrey LLP

(57) ABSTRACT

The present invention relates to the use of compositions comprising trans-clomiphene for treating wasting, especially a loss of muscle mass. The invention is also directed to methods for treating wasting in a patient with chronic obstructive pulmonary disorder. The present invention is also directed to methods for treating hypogonadism in males with chronic obstructive pulmonary disorder.

6 Claims, 6 Drawing Sheets